(12) United States Patent
Weiszl et al.

(10) Patent No.: US 8,584,693 B2
(45) Date of Patent: Nov. 19, 2013

(54) DEVICE FOR MONITORING GAS CONCENTRATION AND METHOD USING THE DEVICE

(75) Inventors: Gunther Weiszl, Wiener Neudorf (AT); Andrew Richard Thomas Tatarek, Aldershot (GB); Christian Romako, Loosdorf (AT)

(73) Assignee: Linde Aktiengesellschaft, Munich (DE)

( * ) Notice: Subject to any disclaimer, the term of this patent is extended or adjusted under 35 U.S.C. 154(b) by 133 days.

(21) Appl. No.: 13/205,669

(22) Filed: Aug. 9, 2011

(65) Prior Publication Data

US 2012/0192956 A1 Aug. 2, 2012

(30) Foreign Application Priority Data

Aug. 13, 2010 (GB) .................................. 1013623.2

(51) Int. Cl.
*G05D 11/00* (2006.01)

(52) U.S. Cl.
USPC ........................... 137/100; 137/88; 137/87.04

(58) Field of Classification Search
USPC .............. 137/88, 87.04, 87.06, 100, 113, 111
See application file for complete search history.

(56) References Cited

U.S. PATENT DOCUMENTS

| | | | |
|---|---|---|---|
| 2,094,192 A * | 9/1937 | Schmidt | 137/3 |
| 3,273,582 A * | 9/1966 | Valentine | 137/111 |
| 3,727,627 A | 4/1973 | Bird et al. | |
| 4,191,952 A * | 3/1980 | Schreiber et al. | 340/611 |
| 4,328,823 A | 5/1982 | Schreiber | |
| 4,442,856 A | 4/1984 | Betz | |
| 4,602,653 A | 7/1986 | Ruiz-Vela et al. | |
| 4,770,094 A * | 9/1988 | Schiel | 100/163 A |
| 5,335,652 A | 8/1994 | Falb et al. | |
| 5,411,019 A | 5/1995 | Smith | |
| 5,537,993 A | 7/1996 | Reichert et al. | |
| 5,576,498 A | 11/1996 | Shambayati | |
| 2008/0066752 A1 | 3/2008 | Baker et al. | |

FOREIGN PATENT DOCUMENTS

| | | |
|---|---|---|
| GB | 1 571 023 | 7/1980 |
| GB | 2 240 849 A | 8/1991 |
| WO | WO 2006/130369 A2 | 12/2006 |
| WO | WO 2008/112423 A1 | 9/2008 |

OTHER PUBLICATIONS

International Search Report for PCT/GB2011/001203, Date of Mailing: Nov. 18, 2011, Authorized Officer: John Loughman, 13 pp.

* cited by examiner

*Primary Examiner* — Stephen M Hepperle
*Assistant Examiner* — R. K. Arundale
(74) *Attorney, Agent, or Firm* — David A. Hey (57) ABSTRACT

A monitoring apparatus for monitoring the relative flow rates of first and second gases that are to be mixed comprises a first flow-monitoring, laminar flow element in a first gas flow path for detecting a differential first gas pressure thereacross and a second flow-monitoring, laminar flow element in a second gas flow path for detecting a differential second gas pressure thereacross. A comparator device compares the differential pressures and is operable to generate a response in dependence on said comparison.

35 Claims, 6 Drawing Sheets

DEVICE FOR MONITORING GAS CONCENTRATION AND METHOD USING THE DEVICE

FIELD OF THE INVENTION

The invention relates to devices for monitoring gas concentration, more particularly but not exclusively for detecting gas concentrations in the case of gases for which certain concentrations are considered critical.

BACKGROUND TO THE INVENTION

The concentration of a given gas may be important in many different fields. One such field is the use of medical gases, where the correct concentration may be critical from the point of view of the efficacy and/or safety of administration of the gas to a patient. For example, nitrous oxide is used in admixture with oxygen, typically as a 50/50 mixture, for short anaesthetic applications. It is extremely good, giving almost immediate pain relief, and flushes out of the body very quickly. In some countries the use of a pre-mixed gas is allowed, which permits a mixture of precisely known proportions to be used. In other countries, notably the USA, the use of pre-mixed gas is not permitted. In those circumstances, oxygen and nitrous oxide can be supplied separately and mixed on demand in a mixing device. It is important, however, that the correct proportions of the gases are mixed, the departure of the proportion of oxygen from the target level of 50%, according to standards, being limited to +/−5%. Furthermore, in the event of the proportion of oxygen falling below 20% (known as a hypoxic mix), the use of the oxygen-deficient mixture may result in hypoxia, posing a serious risk to the patient's health.

One device that is widely used to match supply of a gas to inhalation is a demand valve, in which the valve opens and closes in response to inhalation by the patent. A number of ways of mixing gases and delivering to a patient on demand are known. A problem encountered with such arrangements is that, in the case of a failure of a gas mixing device resulting in the mix being outside the range set by standards or, in a particularly serious case, being a hypoxic mix, it is not possible to detect the resultant incorrect flows of $N_2O$ and/or $O_2$.

Inline flow indicators are widely used to monitor flow of gases. The flow passes a flow-meter which provides a visual indication of the flow of the gas. Such systems rely upon the vigilance of staff for appropriate action to be taken in the event that the indicator shows a malfunction. Flow-meters are sensitive at low flows of the kind relevant in the medical field, and can indicate leaks. However, especially where used with a valve they are relatively costly, and dynamic movement, for example of the patient receiving the gas, may make it difficult to detect flow during use. Flow-meters can, moreover, be orientation-sensitive, casting doubt upon the reliability of readings, for example if a device is portable and is stood on an uneven surface. "Popping indicators" (indicators that indicate when flow is over a given threshold) will only detect failures reliably when the indicators do not appear on inhalation by the patient. Additionally, it is not straightforward to use flow-meters to generate an audible alarm, or to prompt automatic remedial adjustment of the gas supply, either or both of which would be advantageous.

It is known to monitor the concentration of gases using electrochemical or paramagnetic devices. The known monitors are complex and expensive, requiring in at least some cases a power supply, appropriate software algorithms, and interfaces to other components, whilst further suffering from the disadvantages of need for calibration to achieve reliable readings and battery life. The complexity of the known monitors adds to cost and can make implementation and obtaining regulatory approval more complicated.

There is a need for a device which allows the ratio of two or more gases in a mixture to be monitored simply and reliably in order that any departure from a desired ratio can be recognised. Further, it would be desirable for the device to be compact in order that it can be housed within a small container and is easy to carry. It would be desirable for such a device to give a signal that would be used for either or both of generating an audible alarm and prompting adjustment (which may include switching off) of the gas supply.

SUMMARY OF THE INVENTION

The invention provides a monitoring apparatus for monitoring the relative flow rates of first and second gases that are to be mixed, comprising:

a first gas flow path for the first gas;

a first flow-monitoring device for detecting a parameter relating to the flow of the first gas along the first gas flow path;

a second gas flow path for the second gas;

a second flow-monitoring device for detecting a parameter relating to the flow of the second gas along said second gas flow path; and a comparator device for comparing said parameter relating to the flow of the first gas and said parameter relating to the flow of the second gas; and operable to generate a response in dependence on said comparison.

The generated response may, for example, include one or more responses selected from termination of flow of the second gas, adjustment of flow of the second gas, and generation of an indicator signal, for example an audible alarm. In one preferred embodiment, the comparator device is operable to reduce or terminate flow of the second gas, preferably to terminate the flow of the second gas. In another preferred embodiment, the comparator device is operable both to reduce or terminate flow of the second gas and to generate an indicator signal.

In certain embodiments, the comparator device comprises a valve element which is acted upon by a force derived from said first flow-monitoring device and by a force derived from said second flow-monitoring device. For example, the valve element may comprise a piston member, for example in the form of an axially displaceable pin. In a preferred embodiment the valve element is a spool valve. Advantageously, the force derived from said first flow-monitoring device acts on the valve element in a first direction and the force derived from said second flow-monitoring device acts on the valve element in a second direction opposed to said first direction.

Preferably, the first flow-monitoring device is a first laminar flow element positioned in said first gas flow path and having an upstream side and a downstream side relative to said first gas flow path, the parameter relating to the flow of the first gas being a pressure component. Preferably, the second flow-monitoring device is a second laminar flow element positioned in said second gas flow path and having an upstream side and a downstream side relative to said second gas flow path, the parameter relating to the flow of the second gas being a pressure component. Advantageously, the parameter relating to the flow of each of the first and second gases is a pressure differential. In a preferred apparatus of the invention those pressure components, especially pressure differentials, are used to generate forces which act on a movable valve element.

It is especially preferred that both the first and second flow-monitoring devices are laminar flow elements. In one embodiment, each laminar flow element comprises a planar mesh element, for example a sheet of mesh material, in which there is a multiplicity of channels extending through the sheet of mesh material. The laminar flow element may comprise as a planar mesh element a single sheet of mesh material but it has been found advantageous for the planar mesh element to comprise two or more, preferably a multiplicity of, superimposed sheets of mesh material. The resistance provided by the planar mesh element, and in consequence the pressure differential across the laminar flow element, may be varied by varying the area of the laminar flow element and/or, where the laminar flow element comprises sheets of mesh material, by varying the number and/or thickness of the sheets of mesh material. Typically, the resistance of the laminar flow elements would be of the order of 10% of the gas supply pressure at the maximum anticipated flow through the laminar flow elements i.e. high enough to create a useful pressure drop but not so high that it negatively affects the performance of the gas mixing device. The resistance of the critical gas laminar flow restriction would in practice preferably be arranged to be higher than the resistance of the non-critical gas laminar flow restriction. The ratio of the two resistances controls the flow ratio at which the device triggers.

Laminar flow elements are known for the measurement of gas flow. In contrast to certain other known methods of determining flow rate, in which there is a quadratic relationship between the flow rate and the pressure, a laminar flow element is able to produce a low differential pressure that is linearly proportional to the flow rate. In practice, the laminar flow element operates by making the gas flow through a multiplicity of passages, the dimensions and configuration of which are such that the turbulent flow that normally occurs will be changed into a laminar flow. The relationship between the differential pressure and the volumetric flow measured is linear, making measurements over a large flow range possible. In particular, at low flow rates, the sensitivity of measurement can be much greater where the pressure is linearly proportional to the flow rate. This has the important consequence that the apparatus of the invention can have greater sensitivity at low flow rates, for example in application of the apparatus of the invention in the pediatric area, where flow rates are much lower than normal adult inhalation flow rates and early and accurate recognition of incorrect proportions of the gases is vital. It is a particular advantage of the apparatus of the invention that it can be used over a wide range of flow rates encompassing both the low flow rates encountered in pediatric use and the higher flow rates that might be encountered in use with large adults.

Advantageously, the comparator device comprises a valve element, a first planar drive element connected to said valve element, and a second planar drive element connected to said valve element, the first planar drive element being acted upon by a force derived from the first laminar flow element and the second planar drive element being acted upon by a force derived from the second laminar flow element. Advantageously, said first planar drive element is acted upon in a first direction by a force derived from the pressure at the upstream side of the first laminar flow element and is acted upon in a second, opposed direction by a force derived from the pressure at the downstream side of the first laminar flow element, and said second planar drive element is acted upon in the first direction by a force derived from the pressure at the downstream side of the second laminar flow element and is acted upon in the second, opposed direction by a force derived from the pressure at the upstream side of the second laminar flow element. In that way, the pressure differentials across the first laminar flow element and across the second laminar flow element, correlating respectively to the first gas flow and second gas flow, are compared to one another and a resultant net force acts upon the valve element. The comparator device is arranged such that, if the resultant net force exceeds a threshold value, a response will be generated.

Advantageously, the comparator device includes a biasing device, the biasing device providing a biasing force which must be overcome in order for the response to be generated. For example, the biasing device may comprise a spring, preferably a compression spring. Where the comparator device comprises a biasing device, the net force acting on the valve element needs to be sufficient to overcome the biasing force of the biasing device, as well as the force arising from the first gas flow and any frictional resistance to movement of the valve member, in order for a response to be generated by the comparator device. It is preferred that frictional effects within the device are kept low, for example by any one or more of making the diameter of the valve element small, by otherwise making the contact surface of the valve element with other parts of the device small, and by applying low-friction coatings to the valve member and/or to any surfaces in contact therewith. Additionally, manufacturing the valve member from a light material, for example of aluminium or a light plastics material, helps reduce the resistance to movement.

Preferably, the comparator device comprises a valve element, for example a spool valve, that is operable to permit or deny passage of the first gas through the comparator device in dependence upon the relative flow rates of the first and second gases.

In a particularly preferred embodiment of the invention, the apparatus includes an arrangement for preventing undesired premature triggering of the device when gas supply is started up and/or unnecessary triggering of the device when gas supply is being switched off at the end of treatment. Thus, preferably the apparatus comprises a device for impeding generation of a said response during starting-up and/or switching-off of the flow of the second gas. Advantageously, the device for impeding generation of a said response during starting-up and/or switching-off of the flow of the second gas comprises a device for delaying the impact on the comparator device of a change in said parameter relating to the flow of the second gas along said second gas flow path. Preferably, the device for impeding generation of a said response comprises at least one restriction in a gas path communicating between the second flow-monitoring device and the comparator device. Preferably, there is a first restriction in a first gas path communicating between a first, upstream side of the second flow-monitoring device, preferably a laminar flow element, and the comparator device and a second restriction in a second gas path communicating between a second, downstream side of the second flow-monitoring device, preferably a laminar flow element, and the comparator device. Advantageously, the diameter of said first restriction is smaller than the diameter of said second restriction. That arrangement is particularly advantageous in the preferred case where the flow-monitoring devices are laminar flow elements. In that case, when the second gas is switched on (assuming that the first gas is already flowing in the first gas flow path), there is a large pressure differential as the flow path fills, the initially large pressure differential decreasing rapidly as the gas fills the downstream regions of the flow path and the difference in the restriction sizes, by slightly delaying the impact of changing pressures and especially of the upstream pressure on the comparator device, enables premature triggering of the device to be avoided. Preferably, the device for impeding generation of a said response during starting-up and/or switching-off of the flow of the second gas further comprises a non-return valve for permitting release of a pressure that would otherwise act to generate a response on switching-off.

The combined peak flow rates of the first and second gases are preferably controlled by the inhalation demand of a patient and may be, for example, from 3 to 200 litres/min preferably 5 to 150 litres/min. Lower peak flow rates in the those ranges, for example 3 to 50 litres/min may be applicable to children, whilst an adult patient may inhale at a peak flow rate of, for example, 30 to 150 litres/min.

DETAILED DESCRIPTION OF PREFERRED EMBODIMENTS

Figure 1:
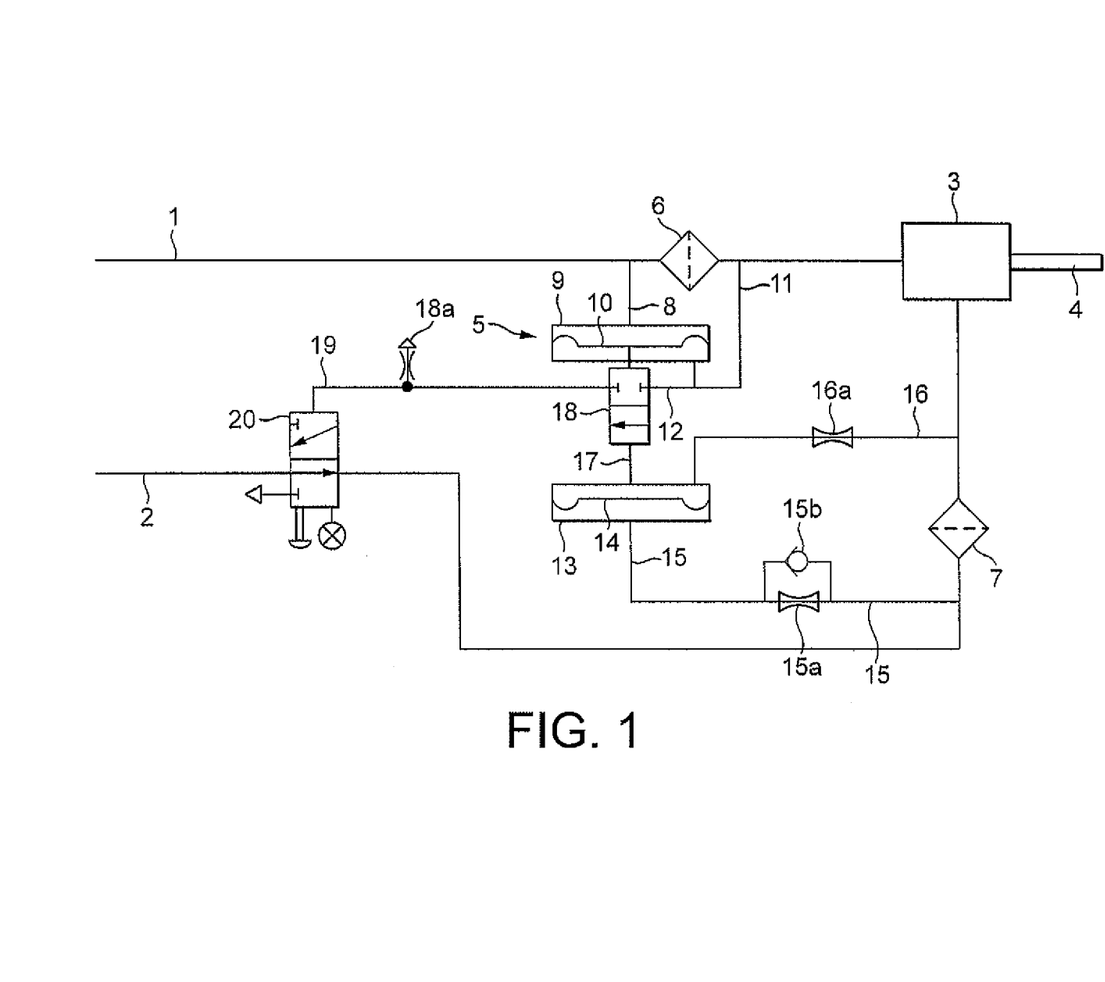
FIG. 1 is a schematic view of a gas supply system including an apparatus according to the invention, with first and second gases flowing within predetermined conditions.

With reference to FIG. 1, a gas system for supply of a mixture of gases comprises a first gas line 1 for carrying a first gas from a first gas source (not shown) and a second gas line 2 for carrying a second gas from a second gas source (not shown). The lines 1 and 2 both communicate with a mixer unit 3 in which the flows of the two gases are combined and delivered into a pipeline 4, which carries a mixture of the two gases to a delivery point (not included in FIG. 1). An adequate flow of the first gas must be maintained at all times, in terms of flow relative to the flow of second gas, in order that the gas mixture in pipeline 4 has required characteristics.

By way of illustration, the gas system of FIG. 1 may be arranged to deliver a mixture of nitrous oxide and oxygen for anaesthetic use by inhalation. In that illustrative example, the first gas would be the oxygen, being the gas whose presence is critical, whilst the second gas would be the nitrous oxide. In the case of use of nitrous oxide for anaesthesia, it is important that the proportion of oxygen in the inhaled mixture (often referred to as $FiO_2$) is maintained within safe limits. The target $FiO_2$ is generally 50% in anaesthetic applications, a level typically used in medical practice. The proportion of $O_2$ in gas line 4 would desirably be maintained within +/−5% of the target $FiO_2$ a level that is specified by relevant industry standards. Additionally, the proportion of oxygen must always be above the critical limit of 20% below which the patient's health may be exposed to serious risk.

A flow comparator device 5 is provided for monitoring the relative flow rates of the first gas, in line 1, and second gas, in line 2. The flow comparator is in communication with a first laminar flow element 6 in line 1 and a second laminar flow element 7 in line 2, for example as described below in more detail with reference to the embodiment shown in FIG. 3. A lateral line 8 communicates at one end with line 1 upstream of laminar flow element 6 and at its other end with a chamber 9 housing a diaphragm member 10. The diaphragm member 10 is movably located within the chamber 9. The line 8 enters the chamber 9 in the upper wall thereof, so that the pressure in line 1 acts, via line 8, on the upper surface of diaphragm member 10. A further lateral line 11 communicates at one end with line 1 at a point close to, and downstream of, laminar flow element 6, and at its other end with the chamber 9. The line 11 enters into the chamber 9 in the bottom wall thereof. As a result of the flow passing through the laminar flow element 6, a pressure differential exists between the upstream line 8 and the downstream line 11. The pressure differential is proportional to the flow rate, thus the net effect on the diaphragm is a pressure proportional to the gas flow in line 1 which therefore generates a force proportional to the flow. It will be appreciated that references herein to upper and lower surfaces of a diaphragm member refer to the surfaces which are shown as being "upper" and "lower" relative to one another in the drawings and it is not necessary for the upper surface to be above the lower surface in practice.

An additional line 12 communicates between line 11 and a valve arrangement further described below.

A second chamber 13, containing a second diaphragm member 14 is in communication in generally analogous manner with the line 2. A line 15 communicates between the lower wall of chamber 13 and the line 2 at a location in line 2 upstream of the laminar flow element 7. A line 16 communicates between the upper wall of chamber 13 and line 2 at a location in line 2 close to, and downstream of, laminar flow element 7. In that manner, the pressure, communicated via line 15 from the region of laminar flow downstream of laminar flow element, acts on the upper surface of diaphragm member 14, and the pressure upstream of laminar flow element 7 is applied to the lower surface of the diaphragm member 14. Reference numeral 15a represents a restrictor and reference numeral 15b represents a non-return valve. Reference numeral 16a represents a restrictor. Restrictors 15a and 16a and non-return valve 15b work in combination to prevent triggering of the device on start-up or switching off as will be described in more detail below with reference to FIG. 3.

Figure 2:
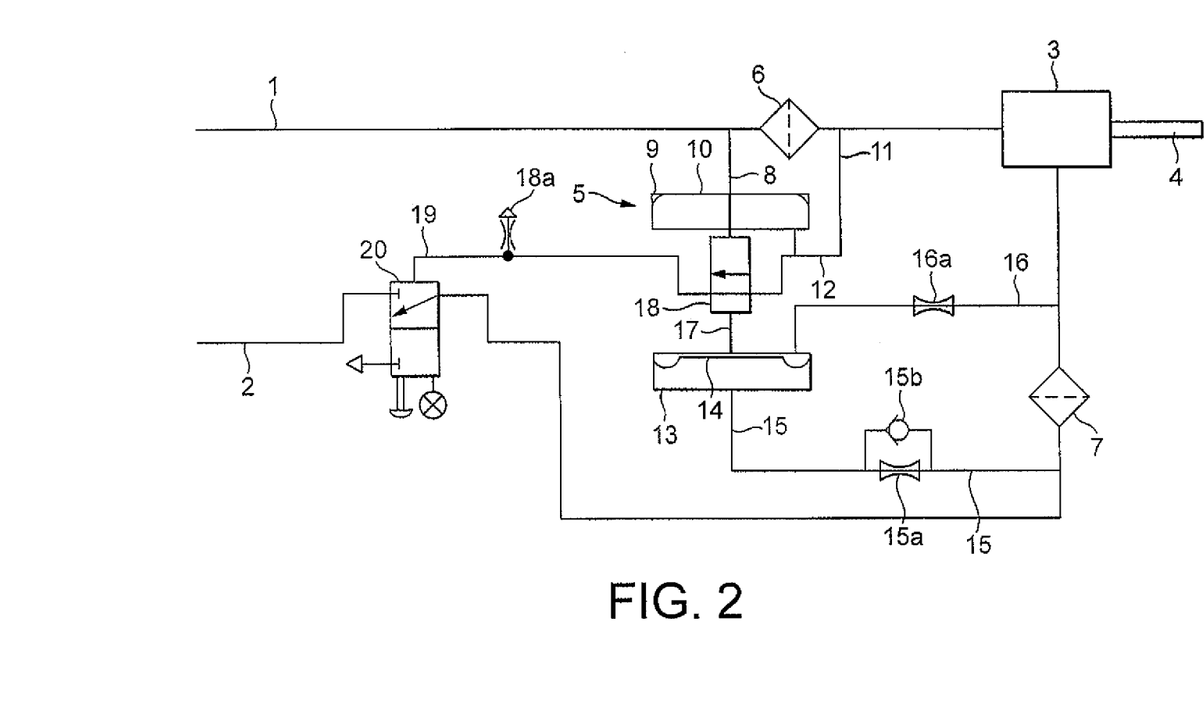
FIG. 2 is a schematic view of the system of FIG. 1 in which a failure has occurred such that the flow rate of the second gas relative to the first exceeds a desirable value.

The diaphragm member 14 and the diaphragm member 10 are pushing on opposed ends of a piston member 17. The piston member 17 is axially movable in dependence upon the relative values of the net force due to the net pressure applied to the diaphragm member 10 arising from the flow in line 1 and the net force due to the net pressure applied to the diaphragm member 14 arising from the flow in line 2. The point at which the piston member 17 starts to move may be affected by the force required to move the piston against piston seals and optionally by further defined force loads, for example, one or more springs (the piston seals and optional loading devices are not shown in FIGS. 1 and 2 but are described in detail below with reference to the embodiment of FIG. 3). The piston forms part of a valve assembly 18. The valve assembly 18 controls a gas path between the line 12 and one end of a line 19. The other end of line 19 communicates with a pressure-piloted shut-off valve 20 provided in line 2. During normal operation, the piston maintains the valve assembly closed so that there is no flow between line 12 and line 19. In the event of the ratio of the flow in line 2 to flow in line 1 exceeding a desired value, the force applied to the diaphragm 14 by virtue of the excess pressure of the second gas causes the piston/diaphragm assembly to move axially as shown in FIG. 2 so as to open the valve 18. That permits the first gas to pass via lines 12 and 19 to actuate shut-off valve 20, which permanently shuts the gas line 1, for example by de-piloting the gas path of the second gas.

If desired, the piston member 17 may be connected to a position indicating element, for example a coloured element, which is operable to indicate the position of the piston member or may be used to trigger an audible alarm.

The valve assembly 18 includes a bleed 18a which serves to avoid false alarms in the event of leakage flows over the valve mechanism reaching the shut-off valve 20. The bleed flow needs to be small compared to the flows encountered when the valve is activated, in order not to affect triggering of any device downstream, but large enough to allow any leaks, for example between the seals and pin, to be vented away without creating a pressure that might cause a false response.

Figure 3:
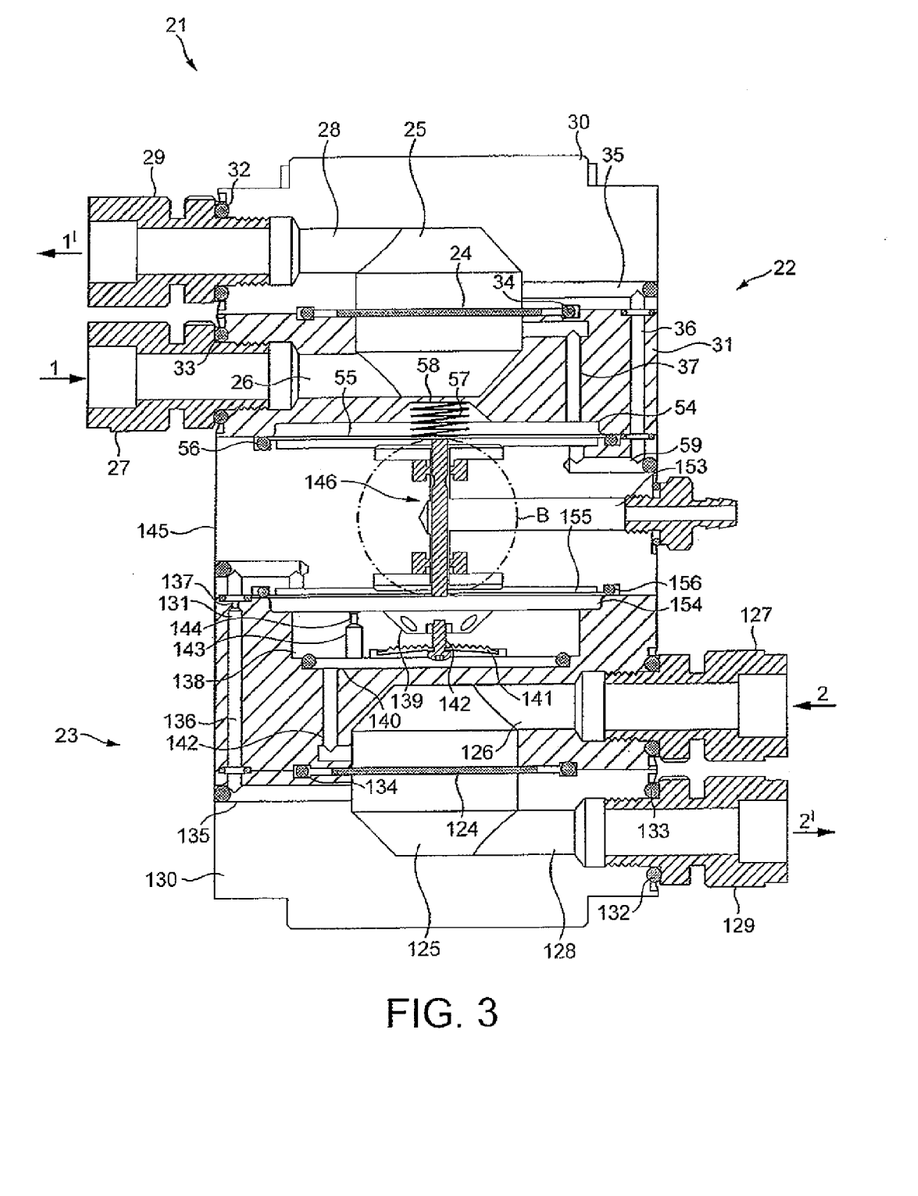
FIG. 3 is an axial section through one embodiment of the apparatus according to the invention suitable for use with supplies of oxygen and nitrous oxide that are to be mixed.

FIG. 3 shows an illustrative embodiment of the apparatus according to the invention. The embodiment of FIG. 3 will be described below with reference to oxygen (as first gas) and nitrous oxide (as second gas) to be mixed for use as a anaesthetic gas. It will be appreciated, however, that other gases may be used in the device shown.

In the embodiment of FIG. 3, the flow comparator device 5, first laminar flow element 6 and second laminar flow element 7 are incorporated in a unit 21. The unit 21 may be of generally cylindrical configuration, the view in FIG. 3 being an axial section. The unit 21 is made up of an oxygen flow portion 22, a nitrous oxide flow portion 23 and a central portion sandwiched therebetween.

The oxygen flow portion 22 includes as laminar flow element 6 a fine mesh sheet 24 centrally located within and extending across a chamber 25. The chamber 25 communicates, on opposite sides of the mesh sheet 24, via channel 26 and inlet 27 with the oxygen supply line 1, and via channel 28 and outlet 29 with the oxygen outlet line 1'. The oxygen flow portion 22 includes outer member 30 and inner member 31 which are fastened together by suitable means such as screw-threaded bolts (not shown). The opposed faces of the members 30 and 31 are provided with respective recessed regions which in the assembled device cooperate to form the chamber 25. The channel 28 extends from the oxygen outlet side of chamber 25, that is, above the mesh 24, substantially radially outwards through the member 30, to the outlet 29. An airtight seal is formed between outlet 29 and the exterior wall of the member 30 by O-ring 32, and a protruding portion of outlet 29 is formed with ridges for providing a friction fit and airtight seal with the line 1'. The channel 26 extends from the oxygen inlet side of chamber 25, beneath the mesh 24, substantially radially outwards through the member 31, and to the inlet 27. An airtight seal is formed between inlet 27 and the exterior wall of the member 31 by O-ring 33, and a protruding portion of inlet 27 is formed with ridges for providing a friction fit and airtight seal with the line 1. For ease of illustration and description, the inlet 27 and outlet 29 and the corresponding channels 26 and 28 are shown in FIG. 3 in the same plane. In practice, however, the inlet 27 may be circumferentially displaced relative to the outlet 29 and channel 26 will then be angularly displaced relative to channel 28.

The mesh sheet 24 is retained in position between the opposed faces of members 30, 31, formation of an airtight seal around the sheet 24 being assisted by means of O-ring 34.

Also provided within member 30 is a bore 35 extending radially from the oxygen outlet side of chamber 25 and arranged to communicate with a perpendicular bore 36 provided in, and extending in the axial direction across, the member 31. As shown in FIG. 3, the outside end of bore 35, like other similar bores in the apparatus, is blocked, for example with a ball bearing or similar. A further bore 37 extends from the oxygen inlet side of chamber 25.

The nitrous oxide flow portion 23 includes as laminar flow element 7 a fine mesh sheet 124 centrally located within and extending across a chamber 125. The chamber 125 communicates, on opposite sides of the mesh sheet 124, via channel 126 and inlet 127 with the nitrous oxide supply line 2, and via channel 128 and outlet 129 with the nitrous oxide outlet line 2'. The nitrous oxide flow portion 23 includes outer member 130 and inner member 131 which are fastened together by suitable means such as screw-threaded bolts (not shown). The opposed faces of the members 130 and 131 are provided with respective recessed regions which in the assembled device cooperate to form the chamber 125. The channel 128 extends from the nitrous oxide outlet side of chamber 125, above the mesh 124 in the orientation shown in FIG. 3, substantially radially outwards through the member 130 to the outlet 129. An airtight seal is formed between outlet 129 and the exterior wall of the member 130 by O-ring 132, and a protruding portion of outlet 129 is formed with ridges for providing a friction fit and airtight seal with the line 2'. The channel 126 extends from the nitrous oxide inlet side of chamber 125, above the mesh 124, substantially radially outwards through the member 131 and to the inlet 127. An airtight seal is formed between inlet 127 and the exterior wall of the member 131 by O-ring 133, and a protruding portion of inlet 127 is formed with ridges for providing a friction fit and airtight seal with the line 2. For ease of illustration and description, the inlet 127 and outlet 129 and the corresponding channels 126 and 128 are shown in FIG. 3 in the same plane. In practice, however, the inlet 127 may be circumferentially displaced relative to outlet 129 and channel 126 will then be angularly displaced relative to channel 128.

The mesh sheet 124 is retained in position between the opposed faces of members 131, 132, formation of an airtight seal around the sheet 124 being assisted by means of O-ring 134. Also provided within member 30 is a bore 135, which is arranged to communicate with a bore 136 provided in, and extending axially across, the member 131. The bore 136 has a restriction 137 at its end remote from the member 130. The member 131 also includes an insert 138, received in a recess in the face of member 131 that is opposed to member 130. The insert 138 provides a non-return gas connection between a recess 139, provided with gas transfer apertures, and a conduit 140 provided in member 131. A flexible planar member 141 is attached to the insert by fixing device 142. The flexible member 141 is deformable in response to an excess pressure in the recess 139, to allow release of gas through the conduit 140, from where it is released via bore 142 to the inlet side of the chamber 125. Under normal operating conditions, the flexible member 141 maintains the non-return connection closed. The force acting on the diaphragm 155 due to the pressure of the non return valve opening needs to be small relative to the frictional force and any spring loading in order to prevent unintended actuation. The opening pressure of the non-return gas connection needs to be such that, during switching off of nitrous oxide with consequent decrease of the pressure in bore 140, the force acting on the diaphragm 155 can (through opening of the non-return valve if the opening pressure is exceeded in the lower part of chamber 154) be maintained small relative to the frictional force and any spring loading acting in opposition thereto.

A further communicating pathway is provided between the nitrous oxide inlet side of the chamber 125 and the remote face of insert 138 via the bore 142, a portion of the conduit 140, and a bore 143 extending in the axial direction through insert 138. The bore 143 is provided with a restriction 144. The restriction 144 is narrower than the restriction 137 for reasons that will be explained further below.

Figure 4A:
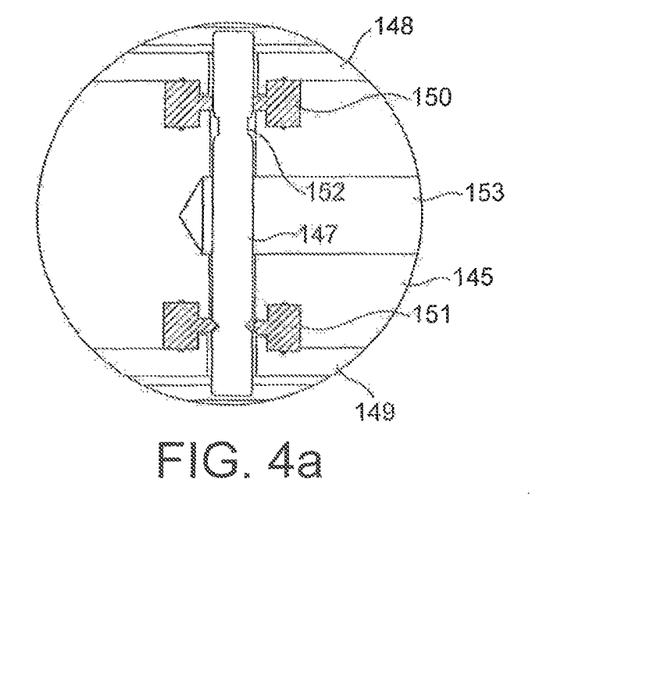
FIG. 4a is a detail of a valve of the apparatus of FIG. 3 showing the valve in the normal operating position in which both gases are flowing through the apparatus at flow rates within the target range.
Figure 4B:
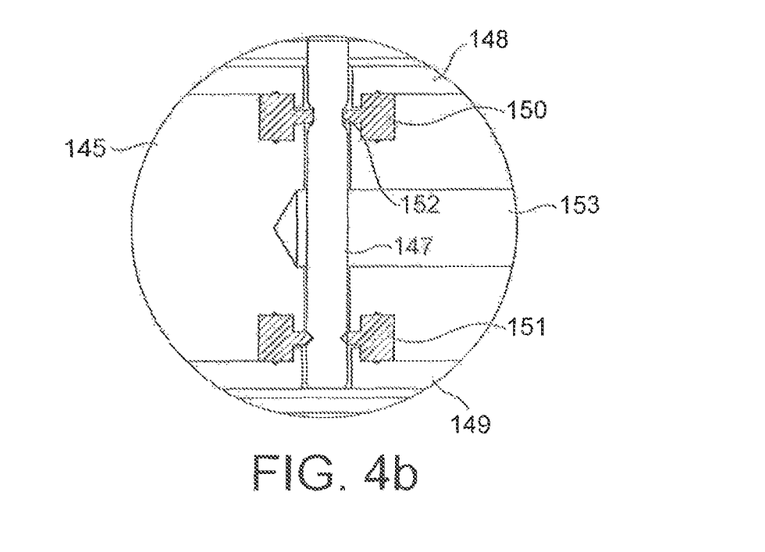
FIG. 4b is a detail of a valve of the apparatus of FIG. 3, with the valve in the position in which the valve is triggered by an excessive proportion of nitrous oxide.

Between the members 31 and 131 is located a central portion 145, incorporating a comparator device for comparing the flow rate of nitrous oxide with the flow rate of the oxygen. The comparator device has a spool valve assembly 146, which is shown in greater detail in FIGS. 4a and 4b which relate to the portion B indicated in FIG. 3. The valve assembly includes a pin 147 which is axially displaceable between the positions shown in FIGS. 4a and 4b in a manner dependent on the relative flow rates of the oxygen and nitrous oxide as will be explained below. The pin is located in two spaced seal retainers 148, 149 and associated lip seals 150 and 151, and is provided with a low-friction coating to facilitate sliding of the pin relative to those components. The pin 147 advantageously has a small diameter to reduce friction. The embodiment of FIG. 3 relies essentially only on two lip seals 150 and 151 to guide the pin 147, which gives rise to only a small frictional resistance to displacement. The pin has a waist 152, which in the normal operating position is axially spaced from the nearest lip seal 150. A bore 153 extends radially from the valve assembly. When a departure from normal operating conditions is detected, the pin is axially displaced such that the waist 152 coincides with the lip seal 150, and provides a pathway for gas from a chamber (not shown in FIGS. 4a and 4b, but located above the seal retainer 148) to the bore 153. Although not illustrated in FIGS. 3, 4a and 4b, the gas exiting via bore 153 may be used for the triggering of a switching device for reducing or stopping the nitrous oxide flow and/or for triggering an alarm.

The lower end of the pin 147 is located in a chamber 154 formed between, and defined by cooperating recesses in, the member 131 and the central member 145. That chamber encloses a diaphragm 155, which is of a very flexible sheet material that is substantially non-porous to oxygen and nitrous oxide, for example a thin sheet of polyurethane or silicone rubber. The diaphragm 155 is retained between circumferentially extending portions of the opposed faces of the member 131 and central member 145, and an airtight seal between those members and the diaphragm is ensured by an O-ring 156. The diaphragm 155, in use, contacts the lower end of pin 147.

The upper end of pin 147 is located in a chamber 54 formed between, and defined by cooperating recesses in, the member 31 and the central member 145. That chamber encloses a diaphragm 55, which is of a very flexible sheet material that is substantially non-porous to oxygen and nitrous oxide. The diaphragm 55 is retained between circumferentially extending portions of the opposed faces of the member 31 and central member 45, and an airtight seal between those members is ensured by an O-ring 56. The diaphragm 55, in use, contacts the upper end of pin 147. Further, a compression spring 57, supported at its upper end on a support surface 58, applies a small biasing force to a central portion of the diaphragm 55 and thence to the upper end of the pin 147. The spring may for example apply a load of 10 to 50 g, preferably 20 to 40 g, for example about 30 g. Upward displacement of the pin 147 requires overcoming of the biasing force of the spring 57 and any friction due to the lip seals 150 and 151 as well as any biasing of the pin arising from response of the diaphragm 55 to the detected oxygen flow rate. The cumulative effects of the spring and friction may be, for example, equivalent to a load of 15 g to 70 g, especially 15 g to 50 g, for example 35 g.

A bore 59 completes a gas pathway from the oxygen outlet side of chamber 25 via bores 35 and 36 to the lower side of chamber 54. The bore 37 communicates with the upper side of chamber 54. In that way, the diaphragm 55 is responsive to the relative pressures upstream and downstream of the laminar flow element 24 and when there is an oxygen flow there is a net load, arising from that differential pressure and proportional to the flow rate, acting on the diaphragm 55 (and thence on pin 147) in the downward direction.

In analogous fashion, the nitrous oxide inlet side of chamber 125 is in communication with the lower part of chamber 154 and the nitrous oxide outlet side of chamber 125 is in communication with the upper part of chamber 154, the diaphragm 155 being responsive to the relative pressures upstream and downstream of the laminar flow element 124. Accordingly, there is a net load, proportional to the nitrous oxide flow rate, acting on the diaphragm 155 (and thence on the pin 147) in the upward direction.

The comparator device is so arranged that, in normal operation, any upward force applied to the pin 147 by diaphragm 155 is insufficient to overcome the cumulative forces biasing the pin in the downward direction (that is, the spring loading and the force attributable to the oxygen flow) and/or any frictional resistance. When, however, there is a reduction in oxygen flow rate, as described below, the upward force on the pin causes axial upward displacement of the pin and triggering of a response as already described with reference to FIGS. 4a and 4b.

The restrictions 137 and 144, serve to delay for a very short time (for example several milliseconds) the response of the diaphragm 155 on starting up of nitrous oxide supply. In practice, oxygen is already flowing in the oxygen side of the apparatus before the nitrous oxide supply is switched on. On switching on of nitrous oxide, there is an initial period, generally of no more than a few milliseconds, in which the nitrous oxide flow path fills. During that period, the pressure in the chamber 154 above diaphragm 155 equalises with the pressure in the chamber 125 downstream of laminar flow element 124 at a rate that is limited by the restriction 137, and the pressure in the chamber below diaphragm 155 equalises with the pressure in the chamber 125 upstream of laminar flow element 124 at a rate that is limited by the restriction 144. Because the restriction 144 is of smaller diameter than the restriction 137, there is a longer time delay in equalisation of the pressure in the chamber below diaphragm 155 with the upstream pressure in the chamber 125. Without the restrictions, the undelayed build up of pressure below the diaphragm 154 would temporarily not be countered by sufficient pressure above the diaphragm 154 with the result that the device may be triggered undesirably before the pressure above the diaphragm 154 reaches the normal operational level. The absolute diameters and relative diameters of the restrictions 137 and 144 are selected so as to be able to prevent premature triggering of the comparator device as just described whilst being sufficiently large to not prevent desired triggering during a failure of the gas mixer, particularly in the case of low flow rates are such as those required for small children. When nitrous oxide supply is switched off, the gas in the upper part of chamber 154 is able to bleed away more quickly through restriction 137 than the gas in the lower part of chamber 154 through restriction 144 as a result of the respective restriction diameters. The non-return valve 141 allows the venting of gas in the lower part of chamber 154 in those circumstances, thereby avoiding undesired triggering of the apparatus as a result of the otherwise transiently high pressure in the lower part of the chamber 154 during switching off.

The laminar flow elements 24, 124 each comprise fine mesh layers defining a multiplicity of channels through which the gas flows, the gas thereby being transformed into a substantially laminar flow. They preferably each comprise a number of superimposed mesh layers. The resistance of the oxygen gas laminar flow restriction is arranged to be higher than the resistance of the nitrous oxide laminar flow restriction. The ratio of the two resistances controls the flow ratio at which the device triggers. Both resistances are kept high enough to generate a useful force for triggering the device but low enough not to interfere with the functioning of the gas mixer, typically in the region of 10% of the supply pressure.

The diaphragms 55, 155 may be of a light, flexible and elastic polymer material, for example 25 μm thick polyurethane film. They may advantageously be provided with a stiffener, which is preferably of a light material for example a light plastics material especially polyester.

In use, the oxygen flow is switched on first, or a pilot flow may be constantly present even when the gas supply is not being used. The nitrous oxide flow is then switched on. The nitrous oxide flow takes a little time, typically less than 1 second, to fill the supply line including the chamber 125 and the line downstream thereof. Before an equilibrium is reached, a temporary excess pressure builds up in the inlet side of chamber 125 and consequently in the lower part of chamber 154. Build-up of the excess pressure in chamber 154 is slowed down by the restrictor 144. Equilibrium is quickly established in the laminar flow elements 24, 124, and the delay in development of the excess pressure in chamber 154 is sufficient to avoid triggering of the comparator device before equilibrium is reached as described above.

Once equilibrium is reached, the laminar flow element 24 provides a pressure drop proportional to the oxygen flow, which, acting on the diaphragm 55, creates a load proportional to the oxygen flow, that load operating axially on the pin 147 in the same direction as the load applied by the spring 57. Similarly, the laminar flow element 124 provides a pressure drop proportional to the nitrous oxide flow, which, acting on the diaphragm 155, creates a load proportional to the nitrous oxide flow, that load operating axially on the pin 147 in the opposite direction to the load applied by the spring 57 and the oxygen flow. In normal operation, the cumulative effects of the biasing spring 57, the oxygen flow rate in line 1 and the frictional forces associated with the lip seals 150 and 151 maintain the pin 147 in the position shown in FIG. 4a. In the event of a failure or reduction in the oxygen supply, the component of the biasing force attributable to the oxygen flow is reduced or eliminated. If the load attributable to the nitrous oxide flow, applied to the pin via diaphragm 155, is sufficient to overcome the remaining opposing load, the pin is axially displaced upwardly to position the waist 152 in line with the lip seal 150, completing a gas path from the lower part of chamber 54 to bore 53 therefore triggering a response which may be in the form of switching off the nitrous oxide supply, as shown in FIG. 1, or may include as well or instead the triggering of an alarm, for example and audible alarm.

Switching off of the nitrous oxide supply is implemented whilst oxygen supply continues. On switching off the nitrous oxide supply, a pressure drop may occur in the outlet side of chamber 125 and the resulting overpressure in the lower part of chamber 154 can be released by means of the non-return connection through insert 143, via flexible member 141 into conduit 140.

Typical illustrative flow rates in the system of the invention are as follows:—
Pediatric use—5 to 50 litre/min
Adult use—30 to 150 litre/min The flow comparator arrangement of the invention offers the opportunity to detect relatively small variations in the concentrations of the gases being mixed, which previously would normally have been detected only with the use of electrochemical or paramagnetic devices, and without detriment to safety. The flow comparator device as described does not require any electrical components, which is an advantage in some circumstances. The inclusion of electrical components, whilst non-preferred in some circumstances, is within the scope of the invention.

Figure 5:
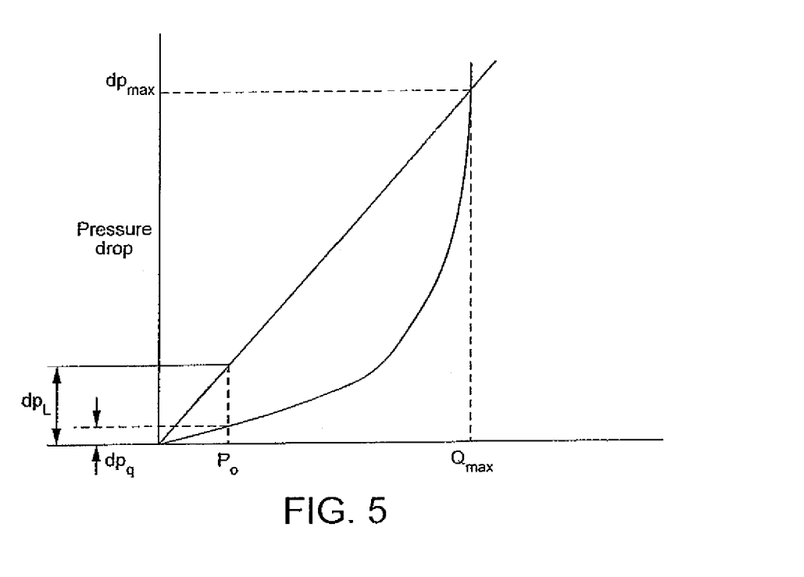
FIG. 5 is a graph showing the relationship between differential pressure and flow rate.

That is made possible in the embodiment described by the use of laminar flow elements. An important characteristic of laminar flow elements is that a laminar flow of the gas is established. The differential pressure Δp (that is, the pressure drop in the gas passing through the laminar flow element) is therefore linearly proportional to the gas flow rate:

$$\Delta p = kq$$

where q is the flow rate and k is a constant. The significance of the linear relationship is apparent from FIG. 5 in which the straight line represents the linear relationship between differential pressure and flow rate in a laminar flow element and the curved line represents the quadratic relationship between pressure and flow rate which applies in other methods for determination of flow rate. At low flow rates, for example those encountered in young children and represented by $P_D$ in FIG. 5, substantial sensitivity benefits are obtained as illustrated by the steeper gradient of the linear relationship in this part of the graph. As a rough guide, the pressure and therefore force available to trigger the valve at a child setting for a given resistance at a peak flow capable of dealing with the demand of a large adult, is typically approximately seven times greater than for a plain orifice. For a given application there will be an acceptable maximum pressure drop dPmax at the maximum flow Qmax, which, for example, may be 10% of the total supply pressure, otherwise the pressure drop may interfere with the function of the gas mixing device.

If two gases X and Y need to be compared, the difference between the differential pressures $\Delta p_y$, $\Delta p_x$ for the two gases can now be calculated. Assuming X is the critical gas (e.g. oxygen in the case of a system for mixing oxygen and nitrous oxide), then the force F available due to flow only to trigger the flow comparator 5 can be determined as the difference between the forces derived from the two pressure drops acting on the respective diaphragms $A_y \Delta p_y - A_x \Delta p_x$ where A is the respective diaphragm area.

Where $F_x$ and $F_y$ are the loads created by the flow rate of gases X and Y on the respective diaphragms:

$$F_x = A_x k_x q_x$$

$$F_y = A_y k_y q_y$$

$$F = F_y - F_x = A_y k_y q_y - A_x k_x q_x$$

In addition to the flows due to force, there are unavoidable frictional loads, R of the seals acting on the pin. Spring loading can be added into the comparator to allow the pin to re-set to the closed position, with the spring force being $F_s$, the trigger point of the valve is represented by the equation:

$$F_y - F_x - F_s R \geq 0$$

Figure 6:
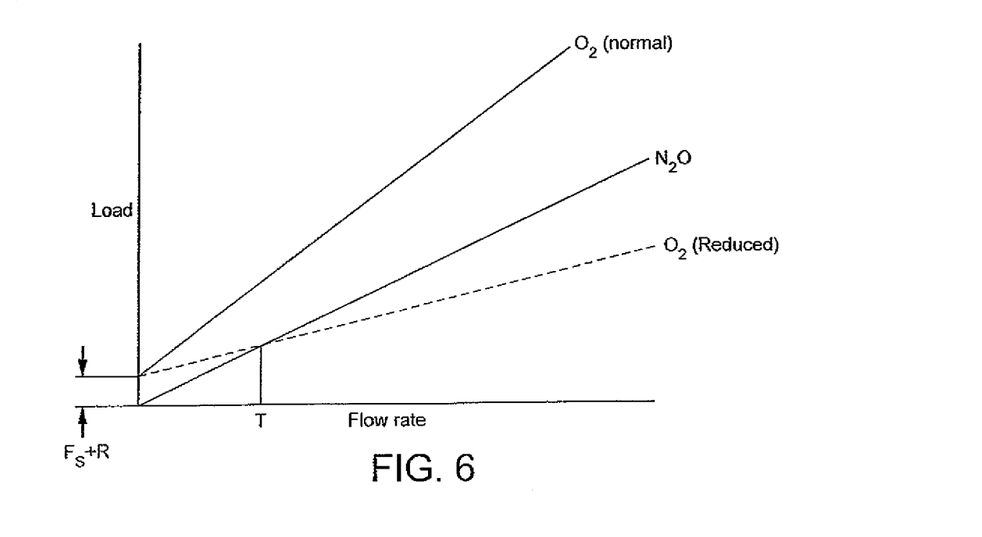
FIG. 6 is a graph illustrating operating and trigger conditions of an apparatus according to the invention.

The above relationship is illustrated in FIG. 6, in which the top two lines represent the load in the comparator device attributable to, respectively, the normal oxygen flow and the nitrous oxide flow, against the flow rate. The third, broken line represents the load due to a reduced oxygen flow which may arise, for example, because of a defect of the gas mixing device, whilst the nitrous oxide flow rate is unaffected. The load offset of the broken line represents the load required to overcome due to the spring bias and any frictional forces, and is represented by the sum:

$$\text{Cumulative load} = F_x + F_s + R$$

This is the load or force that has to be overcome for the device to trigger.

The friction and spring force, while undesirable for sensitivity, have a useful effect in prevention of triggering unintentionally due to vibration or shock, where the pin otherwise might be moved and the device triggered unintentionally. To help vibration or shock resistance, the pin is made in a light material e.g. aluminum or plastic.

The point T represents the minimum nitrous oxide flow rate beneath which the comparator will be triggered at the reduced oxygen flow shown. At normal oxygen flow rates, however, FIG. 6 shows that triggering will not occur.

Figure 7:
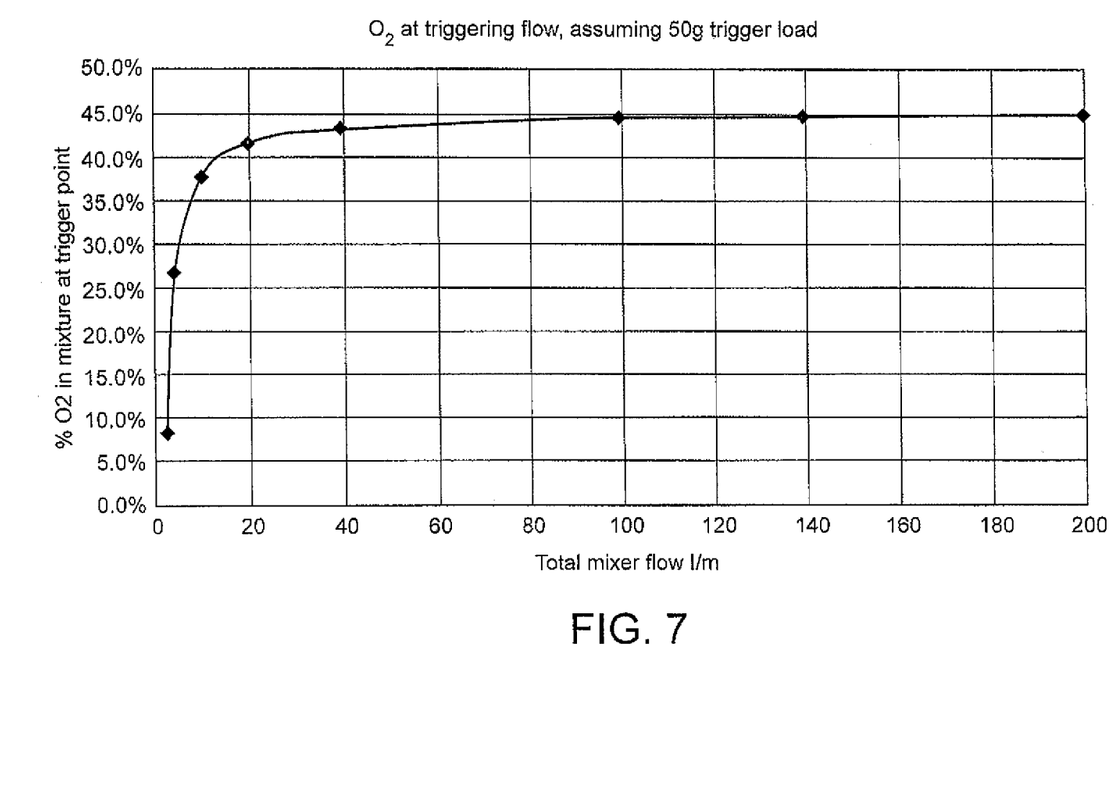
FIG. 7 is a graph illustrating the percentage of oxygen at which the device will trigger at different total flow-rates, for a given ratio of laminar flow element resistances, friction and spring force.

FIG. 7 is a graph showing the proportion of oxygen in a mixture at a trigger point in a particular embodiment according to the invention, having a comparator with a 50 g trigger load. The graph has a very steep gradient, rapidly approaching a substantially constant value for the proportion of oxygen at flow rates of 20 litre/min or greater. This shows that, over a very wide flow rate range, reliable triggering can be obtained. At higher flows, the effects of the friction force and spring force have less effect, so the ratio of flows at which the device will trigger is determined by the ratio of the two laminar flow element resistances.

At lower flows, the effect of friction and spring force become more significant as a percentage of the total forces acting, so the oxygen percentage at triggering falls as flow falls.

As the flows get even smaller, there will come a point where even 100% nitrous oxide will not trigger the comparator, as the force due to nitrous oxide flow will be smaller than the friction and spring load, and therefore is insufficient to move the pin. In practice, however, the apparatus can be so arranged (for example employing various features of construction described above) that that threshold point corresponds to flow rates that are lower than the lowest flow rates anticipated in use of the apparatus.

In the apparatus of the invention the size and resistance of the laminar flow elements, diaphragms, the friction of the pin and the spring, are all selected having regard to the ratio of the smallest peak flow that needs to trigger the comparator, and the largest peak flow that has to flow through the device. For practical purposes, however, the present invention allows for the design of a single device that is capable of accommodating adult flows, while still triggering comfortably above a hypoxic oxygen percentage on child flows.

The invention claimed is:

1. A monitoring apparatus for monitoring the relative flow rates of first and second gases that are to be mixed, comprising:
   a first gas flow path for the first gas;
   a first flow-monitoring device for detecting a parameter relating to the flow of the first gas along the first gas flow path;
   a second gas flow path for the second gas;
   a second flow-monitoring device for detecting a parameter relating to the flow of the second gas along said second gas flow path;
   a comparator device for comparing said parameter relating to the flow of the first gas and said parameter relating to the flow of the second gas; and operable to generate a response in dependence on said comparison, wherein:
   the first flow-monitoring device is a laminar flow element positioned in said first gas flow path and having an upstream side and a downstream side relative to said first gas flow path, the parameter relating to the flow of the first gas being a pressure differential between said upstream and downstream side, and
   the second flow-monitoring device is a laminar flow element positioned in said second gas flow path and having an upstream side and a downstream side relative to said second gas flow path, the parameter relating to the flow of the second gas being a pressure differential between said upstream and downstream sides,
   wherein the comparator device comprises a spool valve.

2. A monitoring apparatus according to claim 1, in which the first flow-monitoring device has a greater resistance to flow than said second resistance to flow.

3. A monitoring device according to claim 1, wherein the response to be generated is selected from reducing or terminating flow of the second gas and triggering an alarm.

4. A monitoring apparatus for monitoring the relative flow rates of first and second gases that are to be mixed, comprising:
   a first gas flow path for the first gas;
   a first flow-monitoring device for detecting a parameter relating to the flow of the first gas along, the first gas flow path;
   a second gas flow path for the second gas;
   a second flow-monitoring device for detecting a parameter relating to the flow of the second gas along, said second gas flow path;
   a comparator device for comparing said parameter relating to the flow of the first gas and said parameter relating to the flow of the second gas; and operable to generate a response in dependence on said comparison, wherein:
   the first flow-monitoring device is a laminar flow element positioned in said first gas flow path and having an upstream side and a downstream side relative to said first gas flow path, the parameter relating to the flow of the first gas being a pressure differential between said upstream and downstream side,
   the second flow-monitoring device is a laminar flow element positioned in said second gas flow path and having an upstream side and a downstream side relative to said second gas flow path, the parameter relating to the flow of the second gas being a pressure differential between said upstream and downstream sides, and
   a device for impeding generation of a said response during starting-up and/or switching-off of the flow of the second gas comprising a device for delaying the impact on the comparator device of a change in said parameter relating to the flow of the second gas along said second gas flow path.

5. A monitoring device according to claim 4, wherein the comparator device comprises a valve element which is acted upon by a force derived from said first flow-monitoring device and by a force derived from said second flow-monitoring device, and the force derived from said first flow-monitoring device acts on the valve element in a first direction and the force derived from said second flow-monitoring device acts on the valve element in a second direction opposed to said first direction.

6. A monitoring device according to claim 4, wherein the comparator device comprises a valve element, a first planar drive element connected to said valve element, and a second planar drive element connected to said valve element, the first planar drive element being acted upon by a force derived from the first laminar flow element and the second planar drive element being acted upon by a force derived from the second laminar flow element.

7. A monitoring apparatus according to claim 6, wherein said first planar drive element is acted upon in a first direction by a force derived from the pressure at the upstream side of the first laminar flow element and is acted upon in a second, opposed direction by a force derived from the pressure at the downstream side of the first laminar flow element, and said second planar drive element is acted upon in a first direction by a force derived from the pressure at the downstream side of the second laminar flow element and is acted upon in a second, opposed direction by a force derived from the pressure at the upstream side of the second laminar flow element.

8. A monitoring apparatus according to claim 4, in which the first flow-monitoring device has a greater resistance to flow than said second resistance to flow.

9. A monitoring apparatus according to claim 4, wherein the comparator device comprises a spool valve.

10. A monitoring apparatus according to claim 4, wherein the comparator device comprises a valve element that is operable to permit and to deny passage of die first gas through the comparator device in dependence upon the relative flow rates of the first and second gases.

11. A monitoring apparatus for monitoring the relative flow rates of first and second gases that are to be mixed, comprising:
   a first gas flow path for the first gas;
   a first flow-monitoring device for detecting a parameter relating to the flow of the first gas along the first gas flow path;
   a second gas flow path for the second gas;
   a second flow-monitoring device for detecting a parameter relating to the flow of the second gas along said second gas flow path;
   a comparator device for comparing said parameter relating to the flow of the first gas and said parameter relating to the flow of the second gas; and operable to generate a response in dependence on said comparison wherein:
   the first flow-monitoring device is a laminar flow element positioned in said first gas flow path and having an upstream side and a downstream side relative to said first gas flow path, the parameter relating to the flow of the first gas being a pressure differential between said upstream and downstream side,
   the second flow-monitoring device is a laminar flow element positioned in said second gas flow path and having an upstream side and a downstream side relative to said second gas flow path, the parameter relating to the flow of the second gas being a pressure differential between said upstream and downstream sides, and
   a device for impeding generation of a said response during starting-up and/or switching-off of the flow of the second gas comprising at least one restriction in a gas path communicating between the second flow-monitoring device and the comparator device.

12. A monitoring device according to claim 11, wherein the comparator device comprises a valve element which is acted upon by a force derived from said first flow-monitoring device and by a force derived from said second flow-monitoring device, and the force derived from said first flow-monitoring device acts on the valve element in a first direction and the force derived from said second flow-monitoring device acts on the valve element in a second direction opposed to said first direction.

13. A monitoring device according to claim 11, wherein the comparator device comprises a valve element, a first planar drive element connected to said valve element, and a second planar drive element connected to said valve element, the first planar drive element being acted upon by a force derived from the first laminar flow element and the second planar drive element being acted upon by a force derived from the second laminar flow element.

14. A monitoring apparatus according to claim 13, wherein said first planar drive element is acted upon in a first direction by a force derived from the pressure at the upstream side of the first laminar flow element and is acted upon in a second, opposed direction by a force derived from the pressure at the downstream side of the first laminar flow element, and said second planar drive element is acted upon in a first direction by a force derived from the pressure at the downstream side of the second laminar flow element and is acted upon in a second, opposed direction by a force derived from the pressure at the upstream side of the second laminar flow element.

15. A monitoring apparatus according to claim 11, in which the first flow-monitoring device has a greater resistance to flow than said second resistance to flow.

16. A monitoring apparatus according to claim 11, wherein the comparator device comprises a spool valve.

17. A monitoring apparatus according to claim 11, wherein the comparator device comprises a valve element that is operable to permit and to deny passage of the first gas through the comparator device in dependence upon the relative flow rates of the first and second gases.

18. A monitoring apparatus for monitoring the relative flow rates of first and second gases that are to be mixed, comprising:
   a first gas flow path for the first gas;
   a first flow-monitoring device for detecting a parameter relating to the flow of the first gas along the first gas flow path;
   a second gas flow path for the second gas;
   a second flow-monitoring device for detecting a parameter relating to the flow of the second gas along said second gas flow path;
   a comparator device for comparing said parameter relating to the flow of the first gas and said parameter relating to the flow of the second gas; and operable to generate a response in dependence on said comparison wherein:
   the first flow-monitoring device is a laminar flow element positioned in said first gas flow path and having an upstream side and a downstream side relative to said first gas flow path, the parameter relating to the flow of the first as being a pressure differential between said upstream and downstream side,
   the second flow-monitoring device is a laminar flow element positioned in said second gas flow path and having an upstream side and a downstream side relative to said second gas flow path, the parameter relating to the flow of the second gas being a pressure differential between said upstream and downstream sides, and
   a device for impeding generation of a said response during starting-up and/or switching-off of the flow of the second pas comprising a first restriction in a first gas path communicating between a first, upstream side of the second flow-monitoring device and the comparator device and a second restriction in a second gas path communicating between a second, downstream side of the second flow-monitoring device, the diameter of said first restriction being smaller than the diameter of said second restriction.

19. A monitoring device according to claim 18, wherein the comparator device comprises a valve element which is acted upon by a force derived from said first flow-monitoring device and by a force derived from said second flow-monitoring device, and the force derived from said first flow-monitoring device acts on the valve element in a first direction and the force derived from said second flow-monitoring device acts on the valve element in a second direction opposed to said first direction.

20. A monitoring device according to claim 18, wherein the comparator device comprises a valve element, a first planar drive element connected to said valve element, and a second planar drive element connected to said valve element, the first planar drive element being acted upon by a force derived from the first laminar flow element and the second planar drive element being acted upon by a force derived from the second laminar flow element.

21. A monitoring apparatus according to claim 20, wherein said first planar drive element is acted upon in a first direction by a force derived from the pressure at the upstream side of the first laminar flow element and is acted upon in a second, opposed direction by a force derived from the pressure at the downstream side of the first laminar flow element, and said second planar drive element is acted upon in a first direction by a force derived from the pressure at the downstream side of the second laminar flow element and is acted upon in a second, opposed direction by a force derived from the pressure at the upstream side of the second laminar flow element.

22. A monitoring apparatus according to claim 18, in which the first flow-monitoring device has a greater resistance to flow than said second resistance to flow.

23. A monitoring apparatus according to claim 18, wherein the comparator device comprises a spool valve.

24. A monitoring apparatus according to claim 18, wherein the comparator device comprises a valve element that is operable to permit and to deny passage of the first gas through the comparator device in dependence upon the relative flow rates of the first and second gases.

25. A monitoring apparatus for monitoring the relative flow rates of first and second gases that are to be mixed, comprising:
   a first gas flow path for the first gas;
   a first flow-monitoring device for detecting a parameter relating to the flow of the first gas along the first gas flow path;
   a second gas flow path for the second gas;
   a second flow-monitoring device for detecting a parameter relating to the flow of the second gas along said second gas flow path;
   a comparator device for comparing said parameter relating to the flow of the first gas and said parameter relating to the flow of the second gas; and operable to generate a response in dependence on said comparison, wherein:
   the first flow-monitoring device is a laminar flow element positioned in said first gas flow path and having an upstream side and a downstream side relative to said first gas flow path, the parameter relating to the flow of the first gas being a pressure differential between said upstream and downstream side, and
   the second flow-monitoring device is a laminar flow element positioned in said second gas flow path and having an upstream side and a downstream side relative to said second gas flow path, the parameter relating to the flow of the second gas being a pressure differential between said upstream and downstream sides,
   wherein the comparator device includes a biasing device, the biasing device providing a biasing force which must be overcome in order for the response to be generated, wherein the biasing device comprises a spring.

26. A gas supply apparatus for supplying a mixture of first and second gases comprising
   a source of a first gas, including a first gas flow path for said first gas;
   a source of a second gas, including a second gas flow path for said second gas;
   a mixing device for mixing said first gas from said first gas flow path and said second gas from said second gas flow path to obtain a gas mixture;
   a gas delivery conduit arranged to deliver said gas mixture; and
   a monitoring apparatus for monitoring the relative gas flows in said first gas flow path and said second gas flow path, wherein the monitoring apparatus comprises:
   a first flow-monitoring device for detecting a parameter relating to the flow of the first gas along the first gas flow path;
   a second flow-monitoring device for detecting a parameter relating to the flow of the second gas along said second gas flow path;
   a comparator device for comparing said parameter relating to the flow of the first gas and said parameter relating to the flow of the second gas; and operable to generate a response in dependence on said comparison;
   the first flow-monitoring device being a laminar flow element positioned in said first gas flow path and having an upstream side and a downstream side relative to said first gas flow path, the parameter relating to the flow of the first gas being a pressure differential between said upstream and downstream side, and
   the second flow-monitoring device being a laminar flow element positioned in said second gas flow path and having an upstream side and a downstream side relative to said second gas flow path, the parameter relating to the flow of the second gas being a pressure differential between said upstream and downstream sides,
   wherein the comparator device comprises a spool valve.

27. A method of controlling supply of a mixture of first and second gases in which a flow of the first gas and a flow of the second gas are, in use combined to generate the mixture, comprising monitoring a parameter relating to the flow rate of the first gas, monitoring that parameter in relation to the flow rate of the second gas, comparing the values of the parameter determined in respect of said first gas and said second gas, and reducing or terminating the flow of the second gas in the event that the ratio of the measured values departs from a predetermined range, wherein the monitoring of a parameter relating to the flow rate of the first gas comprises passing the gas through a first laminar flow element having a first resistance and the monitoring of a parameter relating to the flow rate of the second gas comprises passing the gas through a second laminar flow element having, a second resistance, the parameter relating to flow rate of the first gas is differential pressure at the first laminar flow element, and the parameter relating to flow rate of the second gas is differential pressure at the second laminar flow element,
   wherein comparing the values of the parameter determined in respect of said first gas and said second gas comprises using a spool valve for the comparison.

28. A method according to claim 27, in which the first resistance is greater than the second resistance.

29. A method according to claim 28, wherein the response comprises actuating an alarm.

30. A gas supply apparatus for supplying a mixture of first and second gases comprising
a source of a first gas, including a first gas flow path for said first gas;
a source of a second gas, including a second gas flow path for said second gas;
a mixing device for mixing said first gas from said first gas flow path and said second gas from said second gas flow path to obtain a gas mixture;
a gas delivery conduit arranged to deliver said gas mixture; and
a monitoring apparatus for monitoring the relative gas flows in said first gas flow path and said second gas flow path, wherein the monitoring apparatus comprises:
a first low-monitoring device for detecting a parameter relating to the flow of the first gas along the first gas flow path;
a second flow-monitoring device for detecting a parameter relating to the flow of the second gas along said second gas flow path;
a comparator device for comparing said parameter relating to the flow of the first gas and said parameter relating to the flow of the second gas; and operable to generate a response in dependence on said comparison;
the first flow-monitoring device being a laminar flow element positioned in said first gas flow path and having an upstream side and a downstream side relative to said first gas flow path, the parameter relating to the flow of the first gas being a pressure differential between said upstream and downstream side,
the second flow-monitoring device being a laminar flow element positioned in said second gas flow path and having an upstream side and a downstream side relative to said second gas flow path, the parameter relating to the flow of the second gas being a pressure differential between said upstream and downstream sides, and
a device for impeding generation of a said response during starting-up and/or switching-off of the flow of the second gas comprising a device for delaying the impact on the comparator device of a change in said parameter relating to the flow of the second gas along said second gas flow path.

31. A method of controlling supply of a mixture of first and second gases in which a flow of the first gas and a flow of the second gas are, in use, combined to generate the mixture, comprising monitoring a parameter relating, to the flow rate of the first gas, monitoring that parameter in relation to the flow rate of the second gas, comparing the values of the parameter determined in respect of said first gas and said second gas, and reducing or terminating the flow of the second gas in the event that the ratio of the measured values departs from a predetermined range, wherein the monitoring of a parameter relating to the flow rate of the first gas comprises passing the gas through a first laminar flow element having a first resistance and the monitoring of a parameter relating to the flow rate of the second gas comprises passing the gas through a second laminar flow element having a second resistance, the parameter relating to flow rate of the first gas is differential pressure at the first laminar flow element, and the parameter relating to flow rate of the second gas is differential pressure at the second laminar flow element, and wherein reducing or terminating the flow of the second gas is impeded during starting-up and/or switching-off of the flow of the second gas.

32. A gas supply apparatus for supplying a mixture of first and second gases comprising
a source of a first gas, including a first gas flow path for said first gas;
a source of a second gas, including a second gas flow path for said second gas;
a mixing device for mixing said first gas from said first gas flow path and said second gas from said second gas flow path to obtain a gas mixture;
a gas delivery conduit arranged to deliver said gas mixture; and
a monitoring apparatus for monitoring the relative gas flows in said first gas flow path and said second gas flow path, wherein the monitoring apparatus comprises:
a first flow-monitoring device for detecting a parameter relating to the flow of the first gas along the first gas flow path;
a second flow-monitoring device for detecting a parameter relating to the flow of the second gas along said second gas flow path;
a comparator device for comparing said parameter relating to the flow of the first gas and said parameter relating to the flow of the second gas; and operable to generate a response in dependence on said comparison;
the first flow monitoring device being a laminar flow element positioned in said first gas flow path and having an upstream side and a downstream side relative to said first gas flow path, the parameter relating to the flow of the first gas being a pressure differential between said upstream and downstream side,
the second flow-monitoring device being a laminar flow element positioned in said second gas flow path and having an upstream side and a downstream side relative to said second gas flow path, the parameter relating to the flow of the second gas being a pressure differential between said upstream and downstream sides, and
a device for impeding generation of a said response during starting-up and/or switching-off of the flow of the second gas comprising at least one restriction in a gas path communicating between the second flow-monitoring device and the comparator device.

33. A gas supply apparatus for supplying a mixture of first and second gases comprising
a source of a first gas, including a first gas flow path for said first gas;
a source of a second gas, including a second gas flow path for said second gas;
a mixing device for mixing said first gas from said first gas flow path and said second gas from said second gas flow path to obtain a gas mixture;
a gas delivery conduit arranged to deliver said gas mixture; and
a monitoring apparatus for monitoring the relative gas flows in said first gas flow path and said second gas flow path, wherein the monitoring apparatus comprises:
a first flow-monitoring device for detecting a parameter relating to the flow of the first gas along the first gas flow path;
a second flow-monitoring device for detecting a parameter relating to the flow of the second gas along said second gas flow path;
a comparator device for comparing said parameter relating to the flow of the first gas and said parameter relating to the flow of the second gas; and operable to generate a response in dependence on said comparison;
the first flow-monitoring device being a laminar flow element positioned in said first gas flow path and having an upstream side and a downstream side relative to said first gas flow path, the parameter relating to the flow of the first gas being a pressure differential between said upstream and downstream side, the second flow-monitoring device being a laminar flow element positioned in said second gas flow path and having an upstream side and a downstream side relative to said second gas flow path, the parameter relating to the flow of the second gas being a pressure differential between said upstream and downstream sides, and a device for impeding generation of a said response during starting-up and/or switching-off of the flow of the second gas comprising a first restriction in a first gas path communicating between ea first, upstream side of the second flow-monitoring device and the comparator device and a second restriction in a second gas path communicating between a second, downstream side of the second flow-monitoring device, the diameter of said first restriction being smaller than the diameter of said second restriction.

34. A gas supply apparatus for supplying a mixture of first and second gases comprising a source of a first gas, including a first gas flow path for said first gas;

a source of a second gas, including a second gas flow path for said second gas;

a mixing device for mixing said first gas from said first gas flow path and said second gas from said second gas flow path to obtain a gas mixture;

a gas delivery conduit arranged to deliver said gas mixture; and a monitoring apparatus for monitoring the relative gas flows in said first gas flow path and said second gas flow path, wherein the monitoring apparatus comprises:

a first flow-monitoring device for detecting a parameter relating to the flow of the first gas along the first gas flow path;

a second flow-monitoring device for detecting a parameter relating to the flow of the second gas along said second gas flow path;

a comparator device for comparing said parameter relating to the flow of the first gas and said parameter relating to the flow of the second gas; and operable to generate a response in dependence on said comparison;

the first flow-monitoring device being a laminar flow element positioned in said first gas flow path and having an upstream side and a downstream side relative to said first gas flow path, the parameter relating to the flow of the first gas being a pressure differential between said upstream and downstream side, and the second flow-monitoring device being a laminar flow element positioned in said second gas flow path and having an upstream side and a downstream side relative to said second gas flow path, the parameter relating to the flow of the second gas being a pressure differential between said upstream and downstream sides, wherein the comparator device includes a biasing device, the biasing device providing a biasing force which must be overcome in order for the response to be generated, wherein the biasing device comprises a spring.

35. A method of controlling supply of a mixture of first and second gases in which a flow of the first gas and a flow of the second gas are, in use, combined to generate the mixture, comprising monitoring a parameter relating to the flow rate of the first gas, monitoring that parameter in relation to the flow rate of the second gas, comparing the values of the parameter determined in respect of said first gas and said second gas, and reducing or terminating the flow of the second gas in the event that the ratio of the measured values departs from a predetermined range, wherein the monitoring of a parameter relating to the flow rate of the first gas comprises passing the gas through a first laminar flow element having a first resistance and the monitoring of a parameter relating to the flow rate of the second gas comprises passing the gas through a second laminar flow element having a second resistance, the parameter relating to flow rate of the first gas is differential pressure at the first laminar flow element, and the parameter relating to flow rate of the second gas is differential pressure at the second laminar flow element, wherein comparing the values of the parameter determined in respect of said first gas and said second gas comprises rising a biasing device that provides a biasing force which must be overcome in order for the response to be generated, said biasing device comprising a spring.

* * * * *